(12) United States Patent
Watanabe et al.

(10) Patent No.: US 10,856,751 B2
(45) Date of Patent: Dec. 8, 2020

(54) BLOOD-VESSEL RECOGNITION BLOOD-FLOW MEASUREMENT METHOD

(71) Applicant: OLYMPUS CORPORATION, Tokyo (JP)

(72) Inventors: Takeshi Watanabe, Tokyo (JP); Shintaro Takahashi, Tokyo (JP)

(73) Assignee: OLYMPUS CORPORATION, Tokyo (JP)

( * ) Notice: Subject to any disclaimer, the term of this patent is extended or adjusted under 35 U.S.C. 154(b) by 430 days.

(21) Appl. No.: 15/709,652

(22) Filed: Sep. 20, 2017

(65) Prior Publication Data

US 2018/0008152 A1 Jan. 11, 2018

Related U.S. Application Data

(63) Continuation of application No. PCT/JP2015/059041, filed on Mar. 25, 2015.

(51) Int. Cl.
*A61B 5/026* (2006.01)
*A61B 5/0285* (2006.01)
(Continued)

(52) U.S. Cl.
CPC ............ *A61B 5/026* (2013.01); *A61B 5/0261* (2013.01); *A61B 5/0285* (2013.01); *A61B 10/00* (2013.01); *A61B 8/06* (2013.01); *G01S 15/8979* (2013.01)

(58) Field of Classification Search
CPC ......... A61B 5/026; A61B 5/0261; A61B 8/06; A61B 3/00; A61B 3/18; A61B 5/02; A61B 5/03

See application file for complete search history.

(56) References Cited

U.S. PATENT DOCUMENTS 5,598,841 A 2/1997 Taniji et al.
2005/0254008 A1* 11/2005 Ferguson ............ A61B 3/1025
351/205

(Continued)

FOREIGN PATENT DOCUMENTS

JP H07-092184 A 4/1995
JP H10-085195 A 4/1998
(Continued)

OTHER PUBLICATIONS

Fredriksson et al. 2007 "Laser Doppler Flowmetry—Theoretical Framework" Dept. BioMed. Engin., Linkoping University, Sweden, www.imt.liu.se/bit/ldf/ldfmain.html (Year: 2007).*

(Continued)

*Primary Examiner* — Keith M Raymond
*Assistant Examiner* — Patrick M Mehl
(74) *Attorney, Agent, or Firm* — Scully, Scott, Murphy & Presser, P.C.

(57) ABSTRACT

A blood-vessel recognition blood-flow measurement method including: obtaining a real-time Doppler spectrum by performing a Fourier transform on a temporal waveform of the intensity of scattered light of laser light in a living body; calculating a normalized real-time Doppler spectrum and a normalized zero spectrum; calculating a region spectrum from a subtracted spectrum that is calculated through subtraction of these calculated spectra; calculating a PS reference spectrum by subtracting, from the region spectrum, the maximum value of the region spectrum in a predetermined PS reference region; calculating an average frequency on the basis of a computational spectrum that is obtained by replacing an element of which the PS reference spectrum is negative with zero; and determining a blood flow velocity by comparing the calculated average frequency with a predetermined threshold.

4 Claims, 19 Drawing Sheets

(51) Int. Cl.
*A61B 10/00* (2006.01)
*A61B 8/06* (2006.01)
*G01S 15/89* (2006.01)

(56) References Cited

U.S. PATENT DOCUMENTS

| | | |
|---|---|---|
| 2008/0059098 A1 | 3/2008 | Zhang |
| 2010/0280398 A1 | 11/2010 | Hachiga et al. |
| 2015/0066000 A1 | 3/2015 | An et al. |

FOREIGN PATENT DOCUMENTS

| | | | |
|---|---|---|---|
| JP | 2000-287946 A | 10/2000 | |
| JP | 2000287946 | * 10/2000 | ............. A61B 5/026 |
| JP | 4490807 B2 | 6/2010 | |
| JP | 5234470 B2 | 7/2013 | |
| WO | WO 03/092520 A1 | 11/2003 | |
| WO | WO 2009/081883 A1 | 7/2009 | |

OTHER PUBLICATIONS

Dombrowski et al. 2007 Limnol. Oceanogr. Methods 5:23-33 (Year: 2007).*
Lohwasser et al. 1999 Applied Optics 38:2128-2137 (Year: 1999).*
Wierda et al. 1996 Proc. SPIE 2629 Biomed. Optoelec. Clin. Chem. Biotech. 1996 12 pages (Year: 1996).*
International Search Report dated Jun. 16, 2015 issued in PCT/JP2015/059041.
International Search Report dated Jul. 7, 2015 in PCT/JP2015/062323.
International Search Report dated Jun. 16, 2015 issued in PCT/JP2015/062323.

* cited by examiner

BLOOD-VESSEL RECOGNITION BLOOD-FLOW MEASUREMENT METHOD

CROSS-REFERENCE TO RELATED APPLICATIONS

This is a continuation of International Application PCT/JP2015/059041, with an international filing date of Mar. 25, 2015, which is hereby incorporated by reference herein in its entirety.

TECHNICAL FIELD

The present invention relates to a blood-vessel recognition blood-flow measurement method.

BACKGROUND ART

In surgical treatment of living tissue, it is important for a surgeon to accurately recognize the existence of a blood vessel hidden in the inside of the living tissue and to perform treatment so as to avoid the blood vessel. Thus, surgical treatment devices having a function for optically detecting a blood vessel existing in living tissue have been proposed (for example, see PTL 1). In PTL 1, the amount of blood in the living tissue is measured, and it is determined whether a blood vessel exists on the basis of the measured amount of blood.

CITATION LIST

Patent Literature

{PTL 1} Publication of Japanese Patent No. 4490807

SUMMARY OF INVENTION

According to one aspect, the present invention provides a blood-vessel recognition blood-flow measurement method including: a step of obtaining a real-time Doppler spectrum by performing a Fourier transform on a temporal waveform of the intensity of scattered light produced when laser light is radiated onto a living body; a step of calculating a normalized real-time Doppler spectrum by normalizing the real-time Doppler spectrum by using an average value of the real-time Doppler spectrum in a predetermined normalized region; a step of calculating a normalized zero spectrum by normalizing a zero spectrum measured when laser light is radiated in a state in which a blood flow does not exist, by using an average value of the zero spectrum in a normalized region; a step of calculating a subtracted spectrum by subtracting the normalized zero spectrum from the normalized real-time Doppler spectrum; a step of calculating a region spectrum by extracting, from the subtracted spectrum, a region for integration by using a predetermined integration region; a step of calculating a PS reference spectrum by subtracting, from the region spectrum, the maximum value of the region spectrum in a predetermined PS reference region; a step of obtaining a computational spectrum by replacing an element of which the PS reference spectrum is negative with zero; a step of calculating an average frequency on the basis of the computational spectrum; and a step of determining a blood flow velocity by comparing the calculated average frequency with a predetermined threshold.

DESCRIPTION OF EMBODIMENTS

A blood-vessel recognition blood-flow measurement method according to one embodiment of the present invention will be described below with reference to the drawings.

Figure 1:
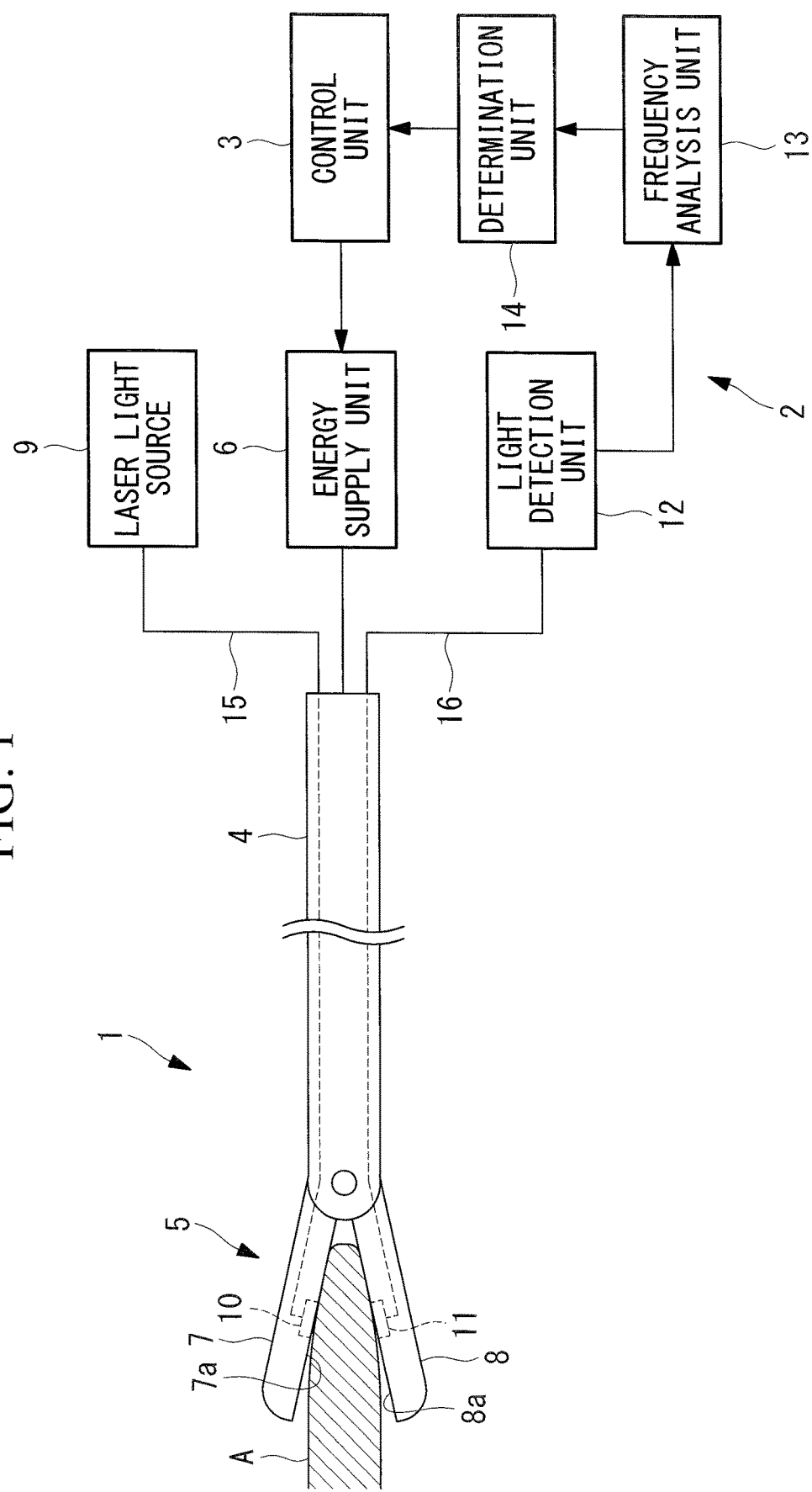
FIG. 1 is a view schematically showing a surgical treatment system to which a blood-vessel recognition blood-flow measurement method according to one embodiment of the present invention is applied.

The blood-vessel recognition blood-flow measurement method of this embodiment is a measurement method performed in a blood-vessel detecting means 2 of a system that is provided with: an energy treatment tool 1 with which living tissue A is treated; the blood-vessel detecting means 2, which optically detects a blood vessel B in the living tissue A; and a control unit 3 that controls the energy treatment tool 1 on the basis of a detection result obtained by the blood-vessel detecting means 2, as shown in FIG. 1.

The energy treatment tool 1 is provided with: an elongated torso portion 4 that can be inserted into the body; an energy action portion 5 that is provided at a distal end of the torso portion 4 and that causes energy to act on the living tissue A; and an energy supply unit 6 that is connected to a base end of the torso portion 4 and that supplies an energy source to the energy action portion 5 via a wire passing through the inside of the torso portion 4.

The energy action portion 5 is energy forceps that have a pair of jaws 7 and 8 capable of gripping the living tissue A (for example, monopolar, bipolar, or grasping forceps capable of supplying an energy source). The upper jaw 7 and the lower jaw 8 have inner surfaces 7a and 8a facing each other. When an energy source (for example, high-frequency current) is supplied from the energy supply unit 6, the upper jaw 7 and the lower jaw 8 produce energy (for example, high-frequency current or ultrasound waves) and radiate the produced energy from the inner surfaces 7a and 8a toward the living tissue A between the inner surfaces 7a and 8a.

The energy action portion 5 has, as operation modes, an incision mode in which the living tissue A is incised with high energy and a coagulation mode in which the living tissue A is coagulated with low energy that is lower than the high energy in the incision mode. The energy action portion 5 switches between the incision mode and the coagulation mode according to the intensity of the energy source supplied from the energy supply unit 6.

The blood-vessel detecting means 2 is provided with: a laser light source 9 that outputs laser light L; a light emitting part 10 that is provided on the inner surface 7a of the upper jaw 7 and that emits the laser light L supplied from the laser light source 9; a light receiving part 11 that is provided on the inner surface 8a of the lower jaw 8 and that receives scattered light S of the laser light L scattered by the living tissue A; a light detection unit 12 that detects the scattered light S received by the light receiving part 11; a frequency analysis unit 13 that obtains time-series data on the intensity of the scattered light S detected by the light detection unit 12 and that applies frequency analysis to the time-series data; and a determination unit 14 that determines the presence or absence of a detection-target blood vessel B that has a diameter in a predetermined range, on the basis of a frequency analysis result obtained by the frequency analysis unit 13.

The laser light source 9 outputs laser light L in a wavelength region (for example, infrared region) that is less absorbed by blood. The laser light source 9 is connected to the light emitting part 10 via an optical fiber 15 passing through the inside of the torso portion 4. The laser light L entering the optical fiber 15 from the laser light source 9 is guided to the light emitting part 10 by the optical fiber 15 and is emitted from the light emitting part 10 toward the inner surface 8a of the lower jaw 8.

The light receiving part 11 is connected to the light detection unit 12 via an optical fiber 16 passing through the inside of the torso portion 4. The scattered light S received by the light receiving part 11 is guided to the light detection unit 12 by the optical fiber 16 and is incident on the light detection unit 12.

The light detection unit 12 converts the intensity of the scattered light S incident from the optical fiber 16 into a digital value and sequentially sends digital values to the frequency analysis unit 13.

Figure 2:
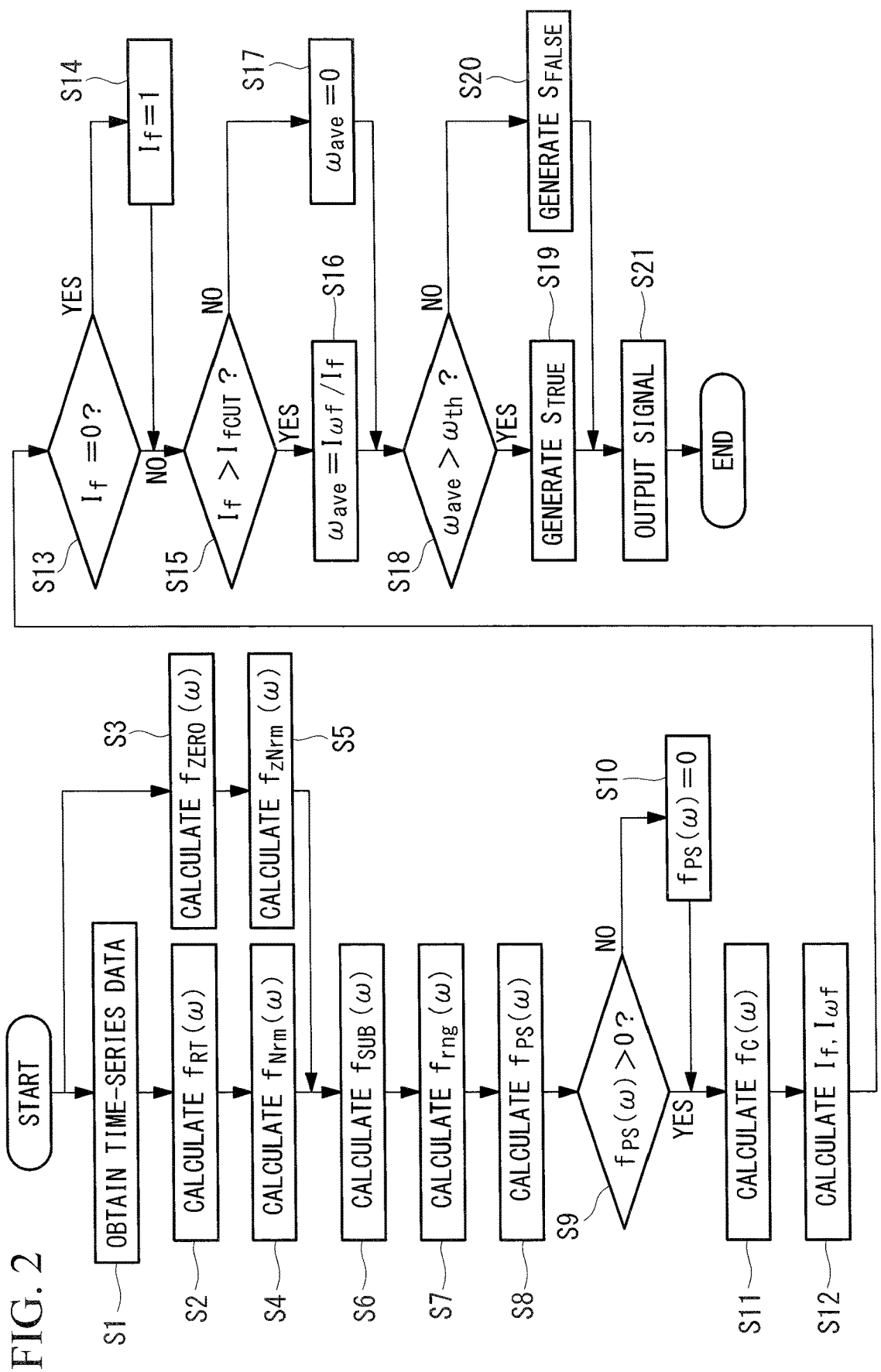
FIG. 2 is a flowchart showing the blood-vessel recognition blood-flow measurement method shown in FIG. 1.

As shown in FIG. 2, the blood-vessel recognition blood-flow measurement method of this embodiment is started such that the frequency analysis unit 13 stores the digital values, which are received from the light detection unit 12, in time series over a predetermined period of time, thereby obtaining time-series data indicating a temporal change in the intensity of the scattered light S (Step S1). The frequency analysis unit 13 applies a fast Fourier transform to the obtained time-series data, thereby calculating a real-time Doppler spectrum $f_{RT}(\omega)$ (Step S2).

Here, the time-series data and the real-time Doppler spectrum $f_{RT}(\omega)$ will be described.

Figure 3:
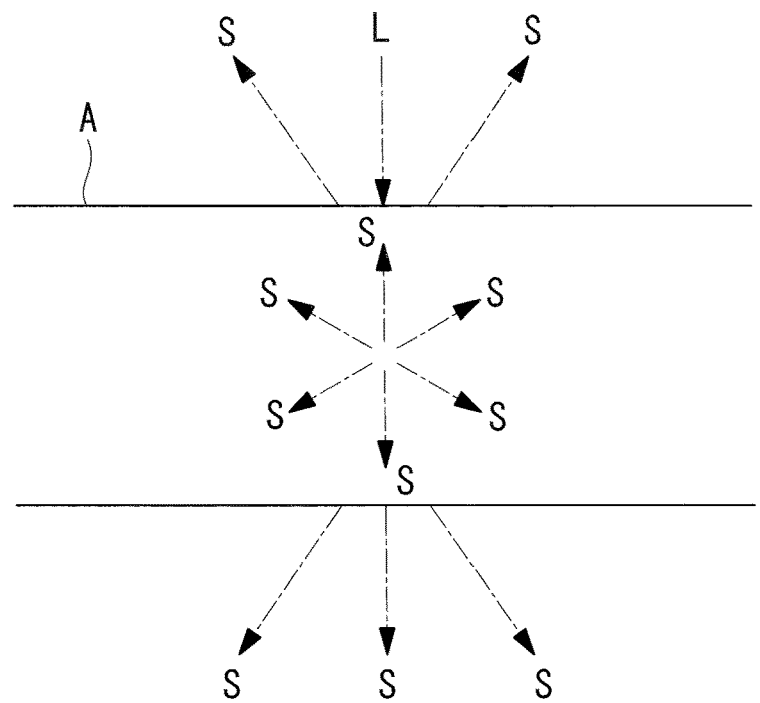
FIG. 3 is a view for explaining scattering of laser light scattered by static components in living tissue.
Figure 4:
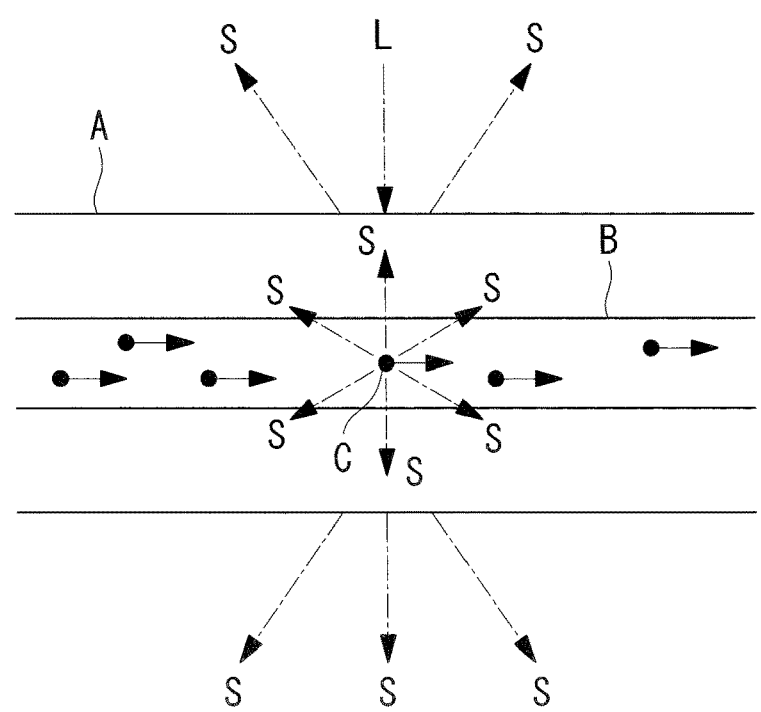
FIG. 4 is a view for explaining scattering of laser light scattered by dynamic components in living tissue.

As shown in FIGS. 3 and 4, the living tissue A includes static components that are static, such as fat and leaking blood leaking from the blood vessel B through bleeding, and dynamic components that are moving, such as red blood cells C in blood that flows in the blood vessel B. When the laser light L having a frequency f is radiated onto the static components, scattered light S having the same frequency f as the laser light L is produced. On the contrary, when the laser light L having the frequency f is radiated onto the dynamic components, scattered light S having a frequency f+Δf that is shifted from the frequency f of the laser light L due to the Doppler shift is produced. The frequency shift Δf at this time depends on the velocity of movement of the dynamic components.

Figure 5:
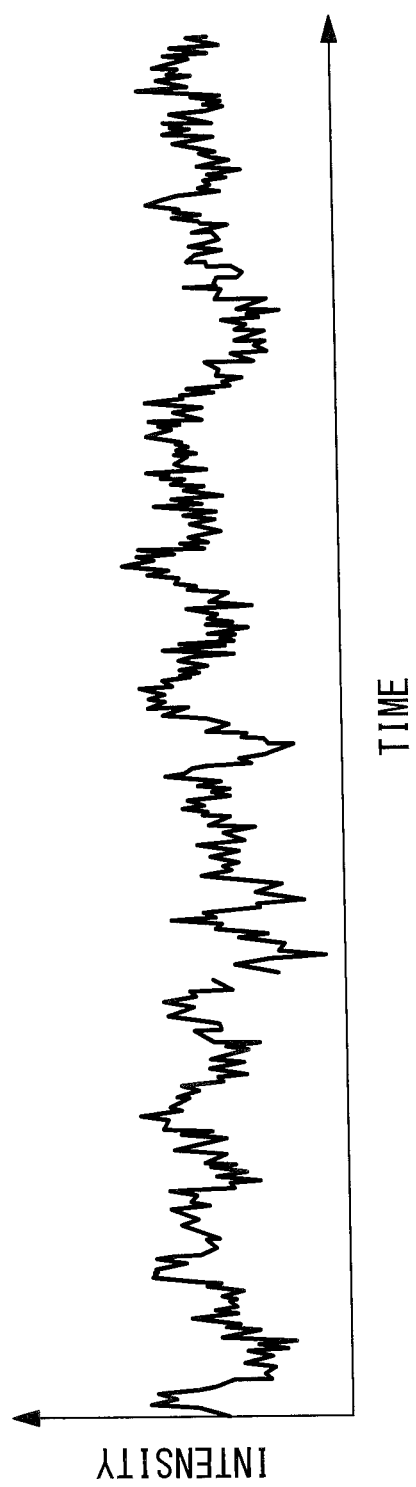
FIG. 5 is a view showing example time-series data of the intensity of scattered light, obtained in a determination unit shown in FIG. 1.

Therefore, when the blood vessel B is included in an area irradiated with the laser light L in the living tissue A, the light receiving part 11 simultaneously receives the scattered light S that is scattered by the blood in the blood vessel B, thus having the frequency f+Δf, and the scattered light S that is scattered by the static components other than the blood in the blood vessel B, thus having the frequency f. As a result, as shown in FIG. 5, the time-series data shows beats in which the intensity of the scattered light S as a whole changes periodically due to the interference of the scattered light S having the frequency f and the scattered light S having the frequency f+Δf.

Because the laser light that has been radiated onto the living tissue A undergoes multiple scattering at the static components and the dynamic components, when the laser light is incident on the red blood cells, the incident angle formed by the direction of travel of the light and the direction of movement of the red blood cells (the direction of a blood flow) is not a single angle but forms a distribution.

Thus, the frequency shift $\Delta f$ due to the Doppler shift forms a distribution. Therefore, the beats of the intensity of the scattered light S as a whole are obtained by multiple frequency components overlapping each other in accordance with the distribution of $\Delta f$. Furthermore, the distribution of $\Delta f$ expands toward the high frequency side as the blood flow velocity becomes high.

Figure 6A:
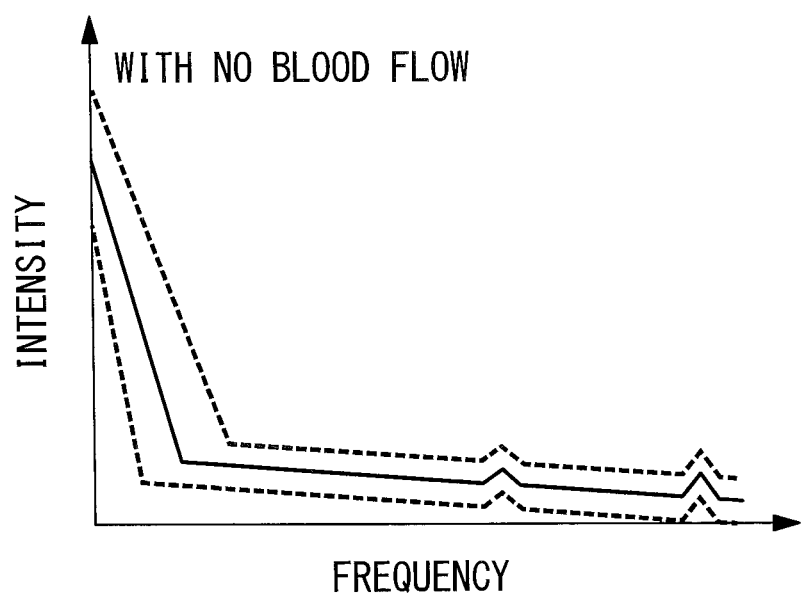
FIG. 6A is a view showing an example real-time Doppler spectrum in a case in which a blood flow does not exist, obtained in the determination unit shown in FIG. 1.
Figure 6B:
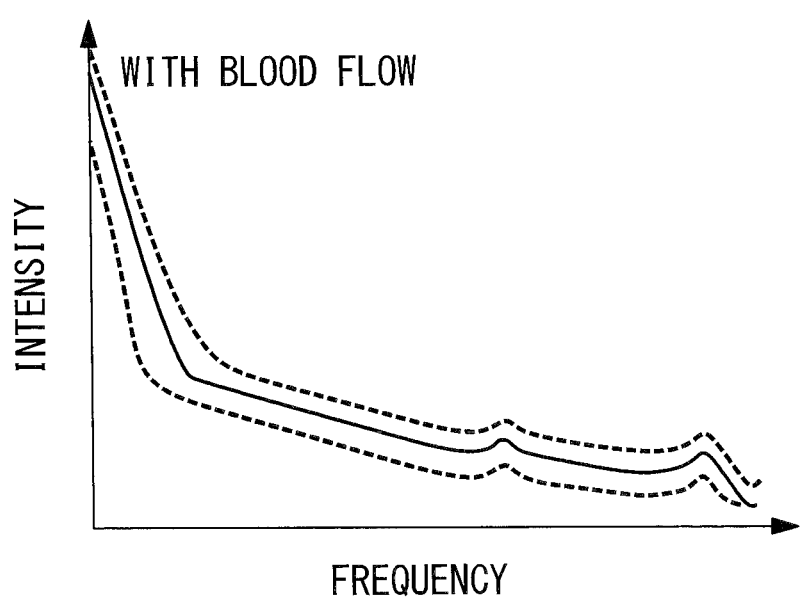
FIG. 6B is a view showing an example real-time Doppler spectrum in a case in which a blood flow exists, obtained in the determination unit shown in FIG. 1.

When the time-series data of such scattered light S is subjected to a fast Fourier transform, as shown in FIGS. 6A and 6B, a real-time Doppler spectrum $f_{RT}(\omega)$ having the intensity at a frequency $\omega$ (hereinafter, the frequency shift $\Delta f$ is referred to as $\omega$) corresponding to the velocity of the blood flow is obtained.

Figure 7A:
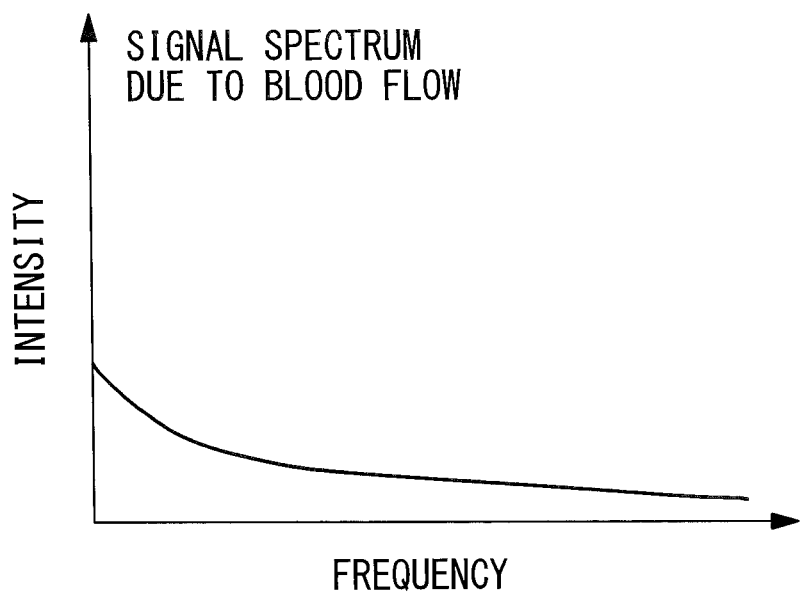
FIG. 7A is a view showing an example signal spectrum due to a blood flow, included in the real-time Doppler spectrum shown in FIGS. 6A and 6B.
Figure 7B:
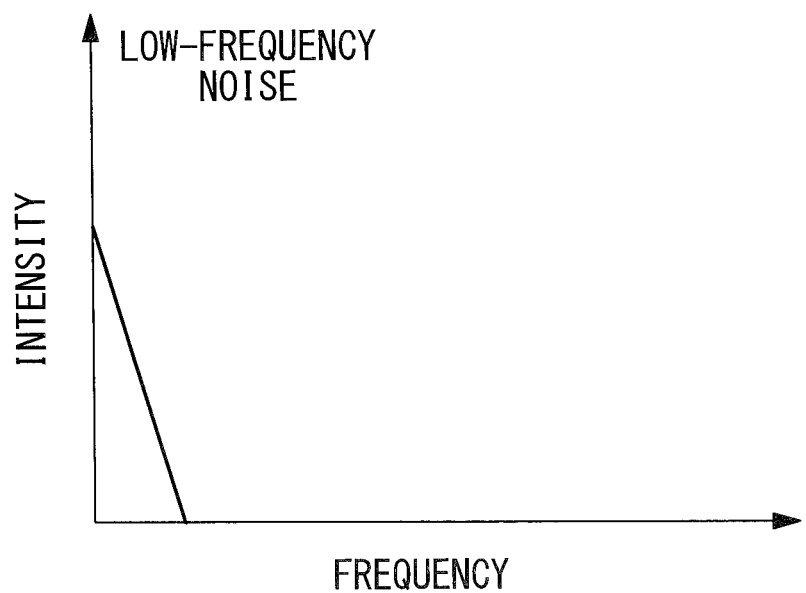
FIG. 7B is a view showing an example of low-frequency noise included in the real-time Doppler spectrum shown in FIGS. 6A and 6B.
Figure 7C:
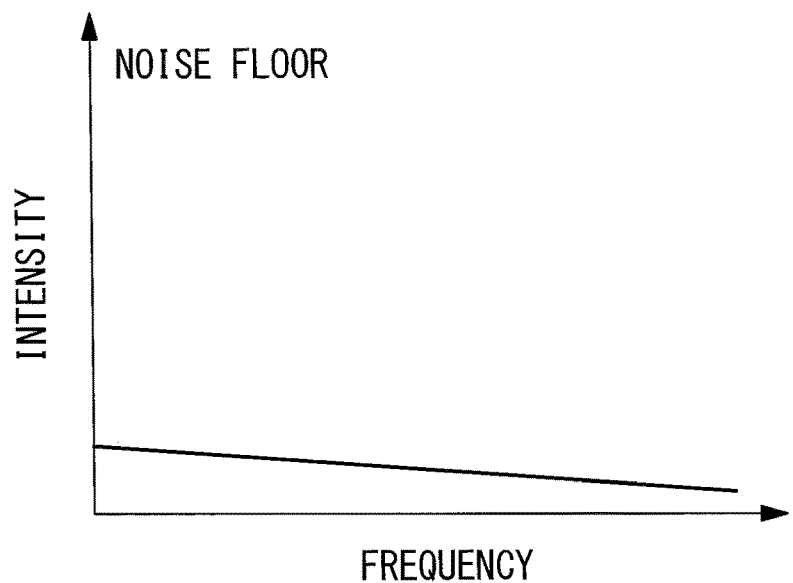
FIG. 7C is a view showing an example of a noise floor included in the real-time Doppler spectrum shown in FIGS. 6A and 6B.
Figure 7D:
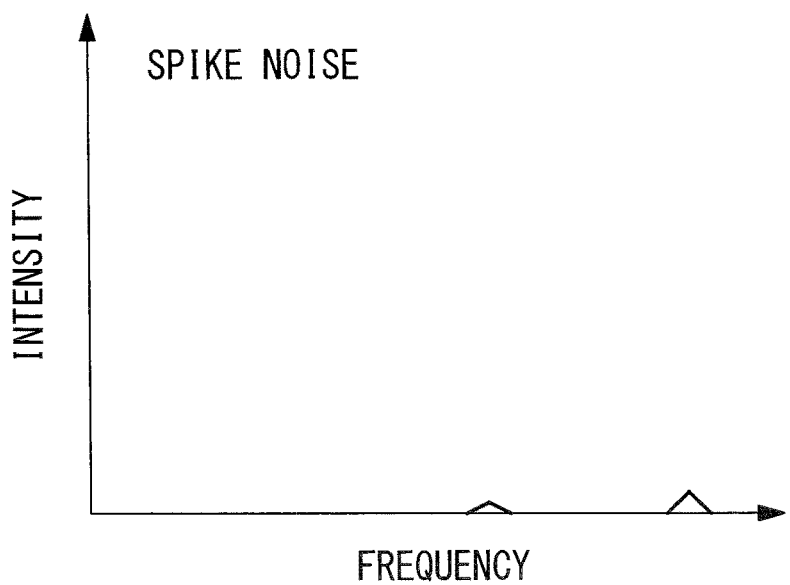
FIG. 7D is a view showing an example of spike noise included in the real-time Doppler spectrum shown in FIGS. 6A and 6B.
Figure 7E:
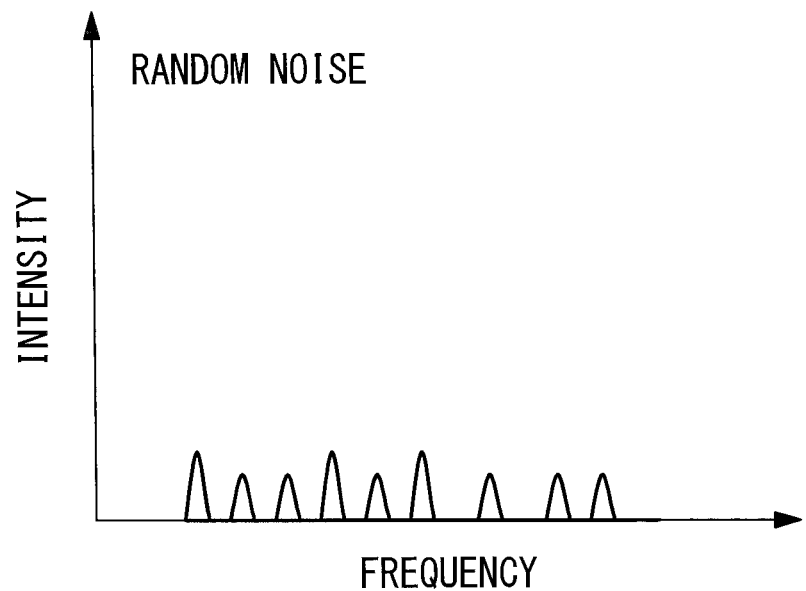
FIG. 7E is a view showing an example of random noise included in the real-time Doppler spectrum shown in FIGS. 6A and 6B.

Here, the real-time Doppler spectrum $f_{RT}(\omega)$ includes, in addition to a signal spectrum due to a blood flow, as shown in FIG. 7A, noise, such as: low-frequency noise that appears, as a change in the real-time Doppler spectrum $f_{RT}(\omega)$, as a result of a fluctuation of the scattering intensity on the unevenness of the surface of or on the boundary of the living tissue A, as shown in FIG. 7B; a noise floor due to light-intensity fluctuation of the laser light source 9 itself, as shown in FIG. 7C; and spike noise that is derived from an electrical system and that appears at specific frequencies, as shown in FIG. 7D. Furthermore, random noise shown in FIG. 7E is also included.

Figure 8A:
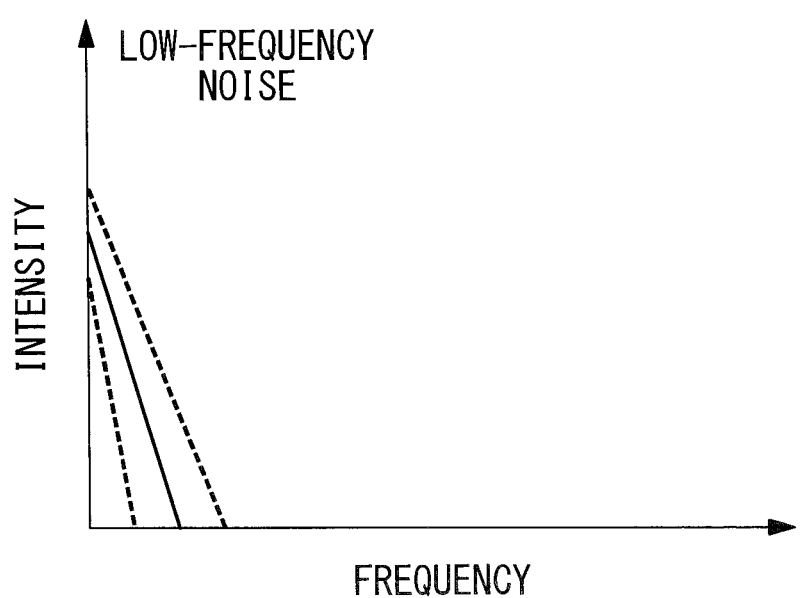
FIG. 8A is a view showing a state in which the low-frequency noise shown in FIG. 7B fluctuates during scanning.
Figure 8B:
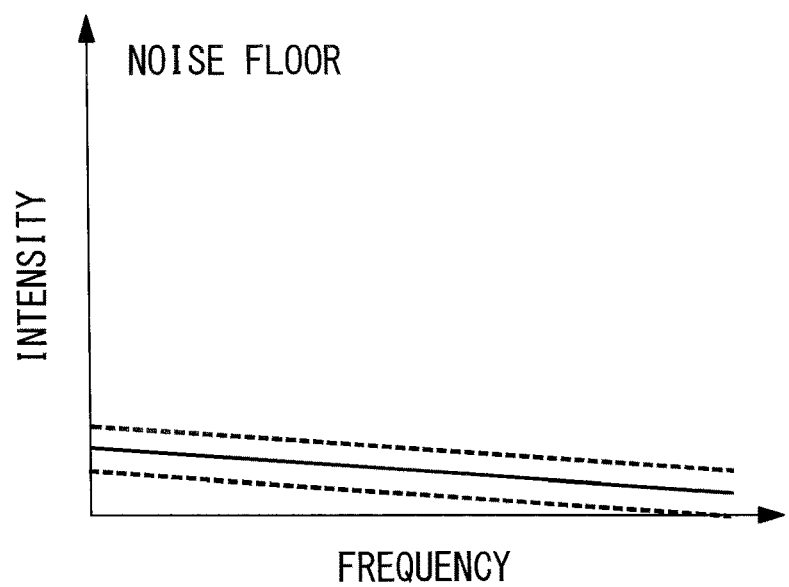
FIG. 8B is a view showing a state in which the noise floor shown in FIG. 7C fluctuates during scanning.

Furthermore, when the energy treatment tool 1 is manually operated, the low-frequency noise and the noise floor fluctuate, as indicated by broken lines in FIGS. 8A and 8B; thus, the real-time Doppler spectrum $f_{RT}(\omega)$ fluctuates as indicated by broken lines in FIGS. 6A and 6B, in either a case in which a blood flow does not exist or a case in which a blood flow exists.

Thus, it is necessary to remove these types of noise to precisely extract the signal spectrum due to a blood flow.

Figure 9:
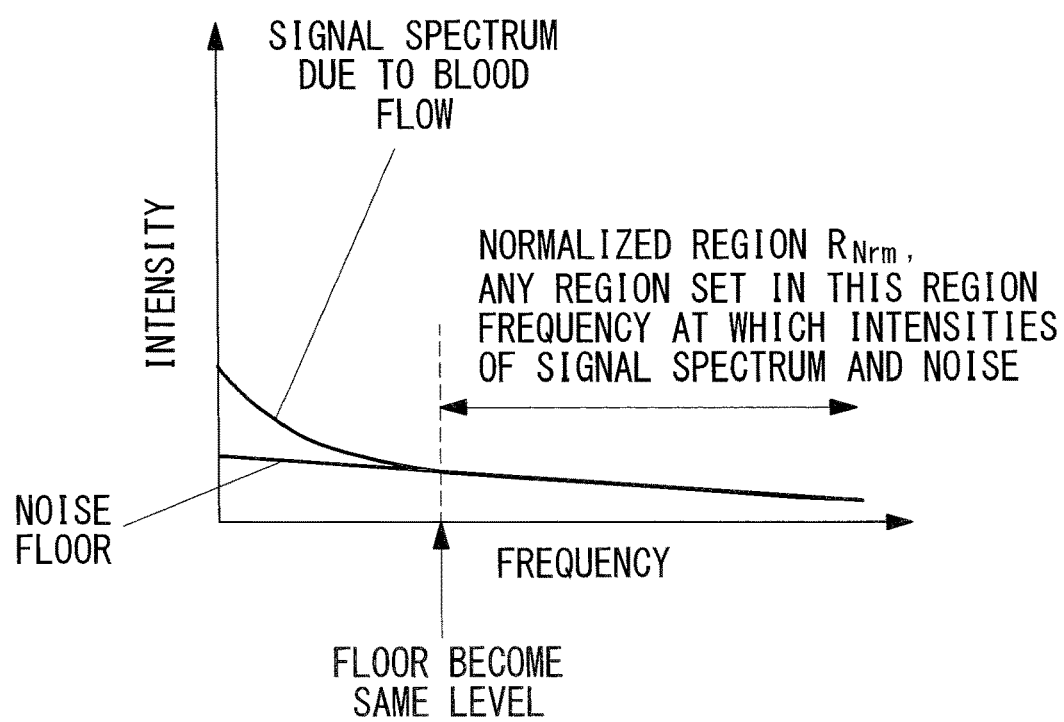
FIG. 9 is a view for explaining the definition of a normalized region used to normalize a spectrum.

In this embodiment, first, a normalized region $R_{Nrm}$ is set in an appropriate frequency range in the real-time Doppler spectrum $f_{RT}(\omega)$. As shown in FIG. 9, the normalized region $R_{Nrm}$ is an arbitrary frequency region set at a frequency higher than the frequency at which the intensity of the real-time Doppler spectrum $f_{RT}(\omega)$ corresponding to a desired blood flow becomes the same level as the noise floor intensity.

Furthermore, a zero spectrum $f_{zero}(\omega)$ that only includes the noise floor and the spectrum is calculated from the scattered-light intensity obtained by radiating the laser light L in a state in which a blood flow does not exist (Step S3).

Next, the real-time Doppler spectrum $f_{RT}(\omega)$ and the zero spectrum $f_{ZERO}(\omega)$ are normalized by using the average value of the real-time Doppler spectrum $f_{RT}(\omega)$ in the normalized region $R_{Nrm}$ (Steps S4 and S5).

Figure 10:
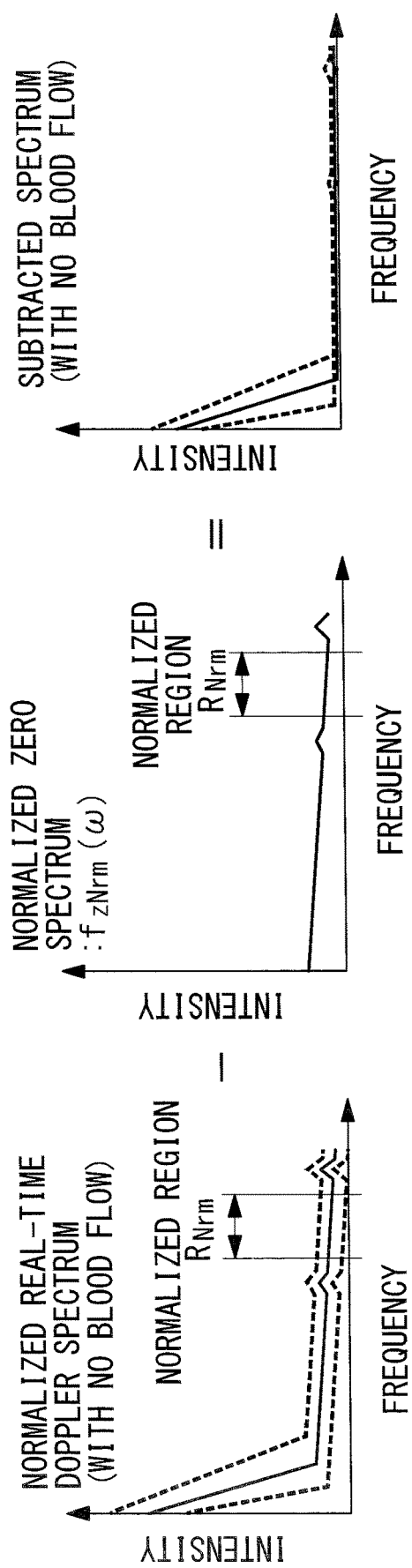
FIG. 10 is a view showing an example subtracted spectrum obtained by subtracting a normalized zero spectrum from a normalized real-time Doppler spectrum in a case in which a blood flow does not exist.
Figure 11:
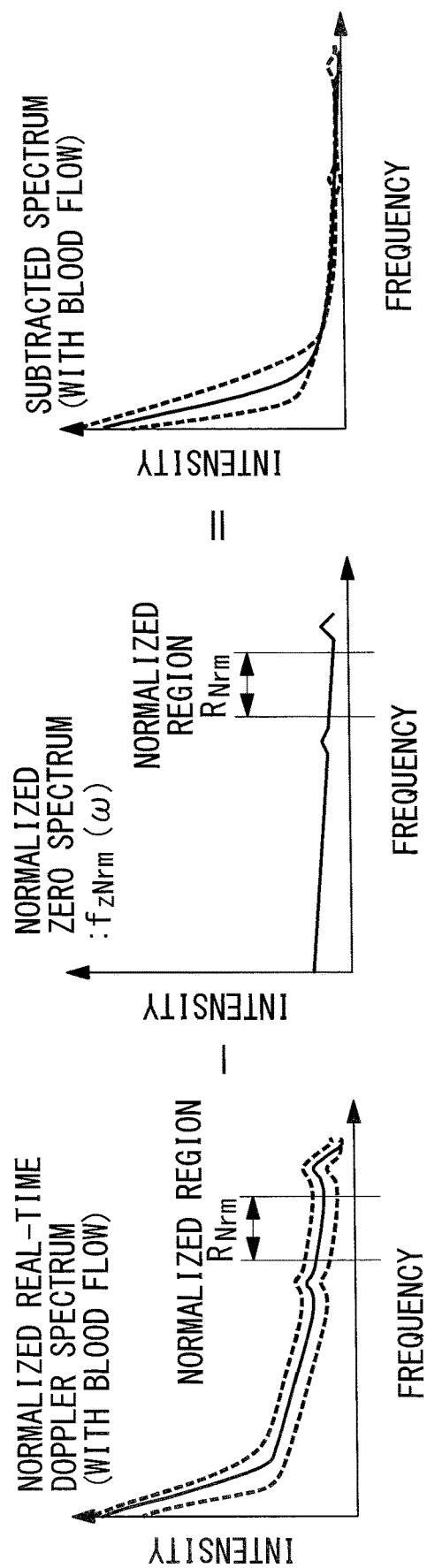
FIG. 11 is a view showing an example subtracted spectrum obtained by subtracting a normalized zero spectrum from a normalized real-time Doppler spectrum in a case in which a blood flow exists.

Then, the normalized zero spectrum $f_{zNrm}(\omega)$ is subtracted from the normalized real-time Doppler spectrum $f_{th}(\omega)$, thereby calculating a subtracted spectrum $f_{SUB}(\omega)$, as shown in FIGS. 10 and 11 (Step S6). Accordingly, the subtracted spectrum $f_{SUB}(\omega)$ in which the noise floor and part of the spike noise have been reduced is calculated.

Figure 12:
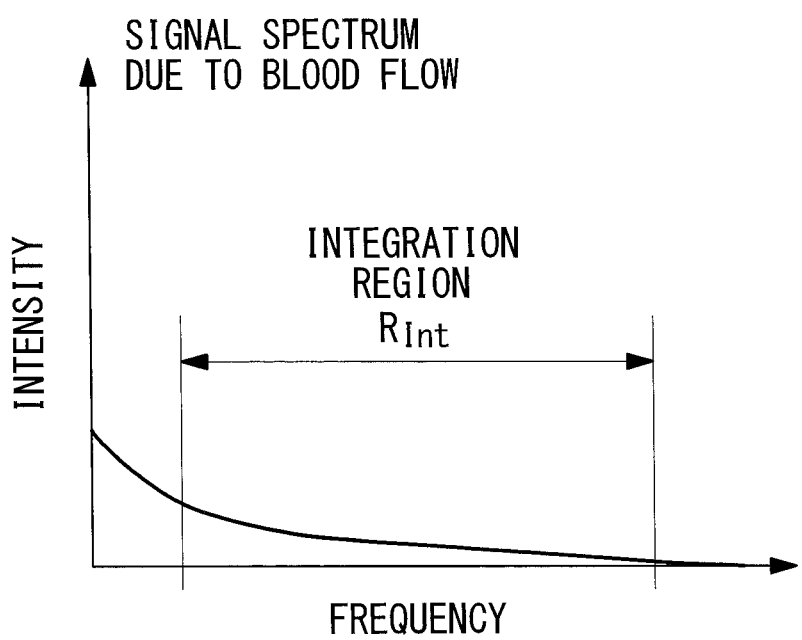
FIG. 12 is a view for explaining the definition of an integration region.
Figure 13A:
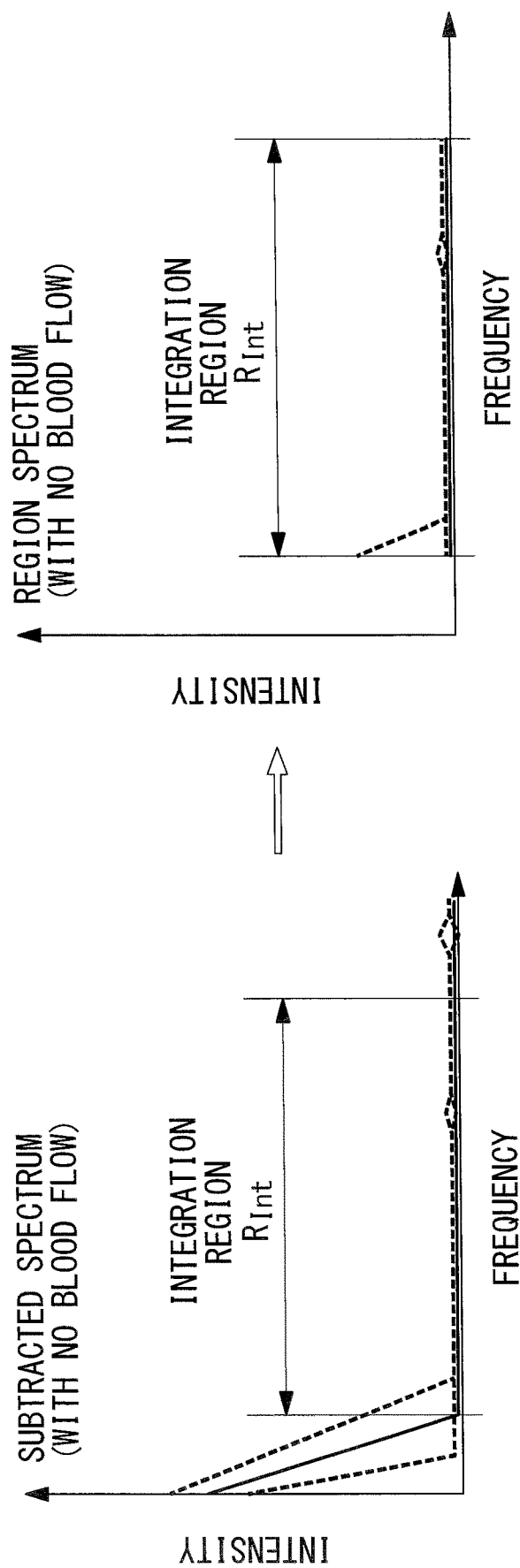
FIG. 13A is a view showing the relationship between the subtracted spectrum and a region spectrum in a case in which a blood flow does not exist.
Figure 13B:
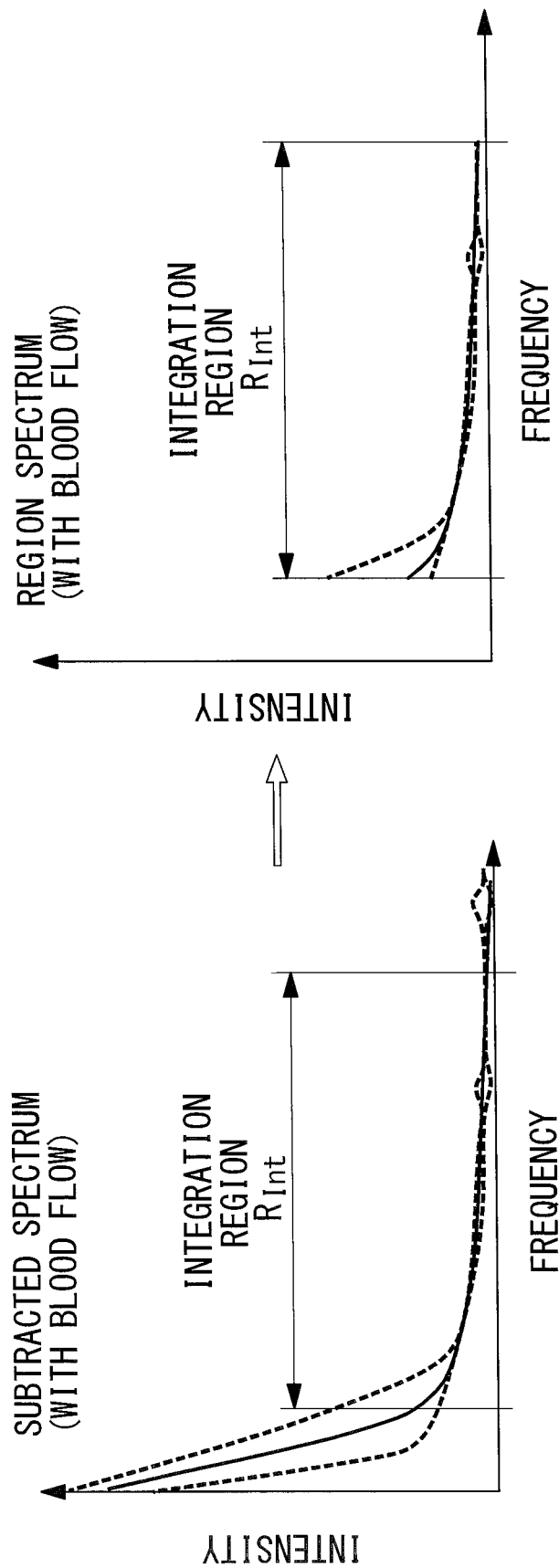
FIG. 13B is a view showing the relationship between the subtracted spectrum and a region spectrum in a case in which a blood flow exists.

Next, an integration region $R_{Int}$ is set such that the region of a signal spectrum due to a blood flow is not cut too much, and the low-frequency noise can be cut, as shown in FIG. 12, and the spectrum in a frequency region lower than the integration region $R_{Int}$ is removed from the subtracted spectrum $f_{SUB}(\omega)$, thereby calculating a region spectrum $f_{rng}(\omega)$, as shown in FIGS. 13A and 13B (Step S7).

Accordingly, the region spectrum $f_{rng}(\omega)$, which is obtained by removing the low-frequency noise and part of the spike noise, is generated.

Figure 14A:
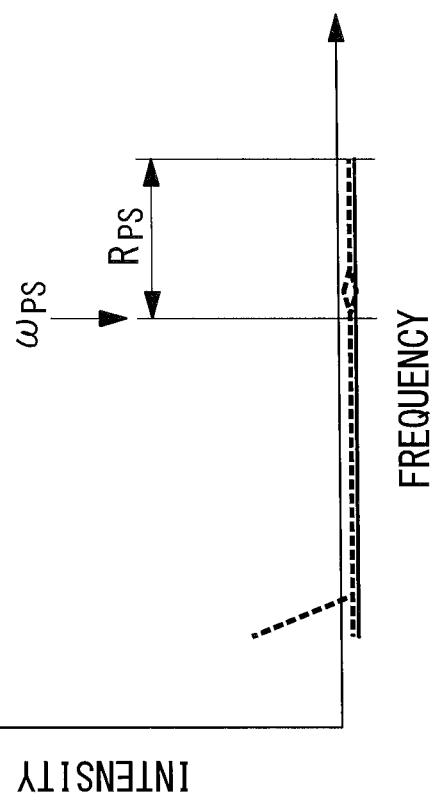
FIG. 14A is a view showing the relationship between the region spectrum and a PS reference spectrum in a case in which a blood flow does not exist.
Figure 14A:
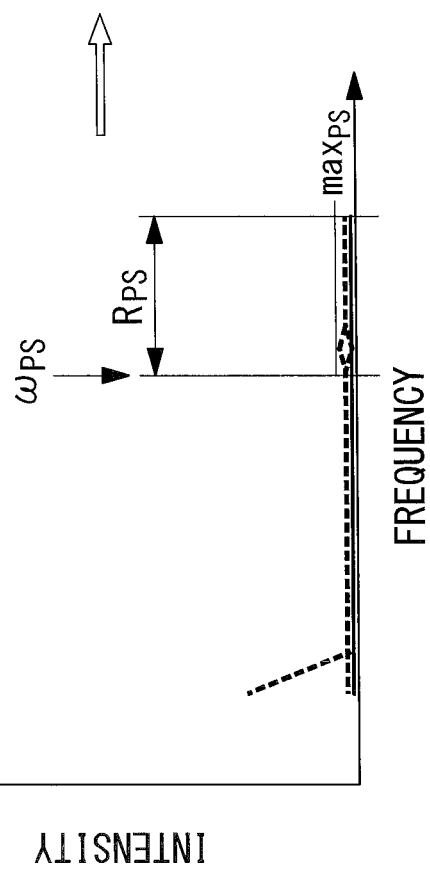
Figure 14B:
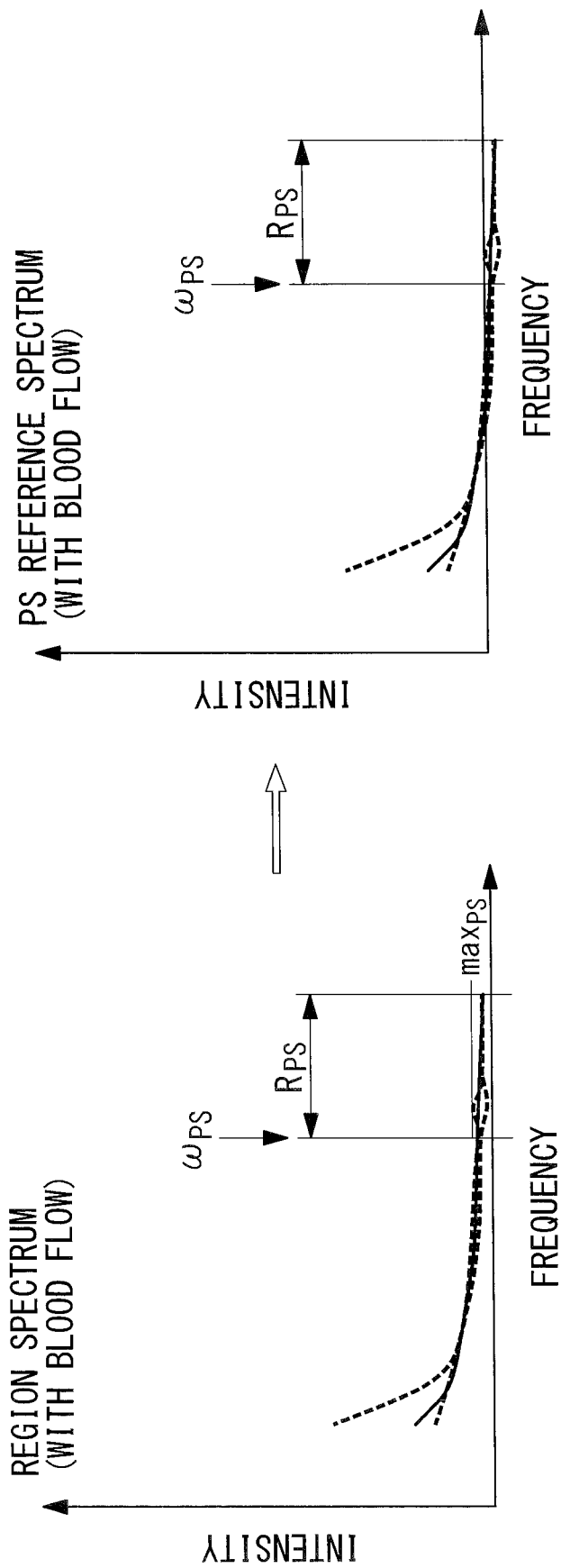
FIG. 14B is a view showing the relationship between the region spectrum and a PS reference spectrum in a case in which a blood flow exists.
Figure 15A:
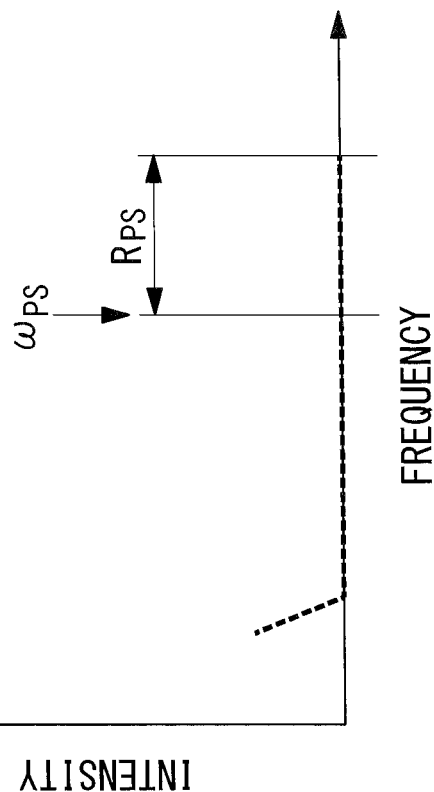
FIG. 15A is a view showing the relationship between the PS reference spectrum and a computational spectrum in a case in which a blood flow does not exist.
Figure 15A:
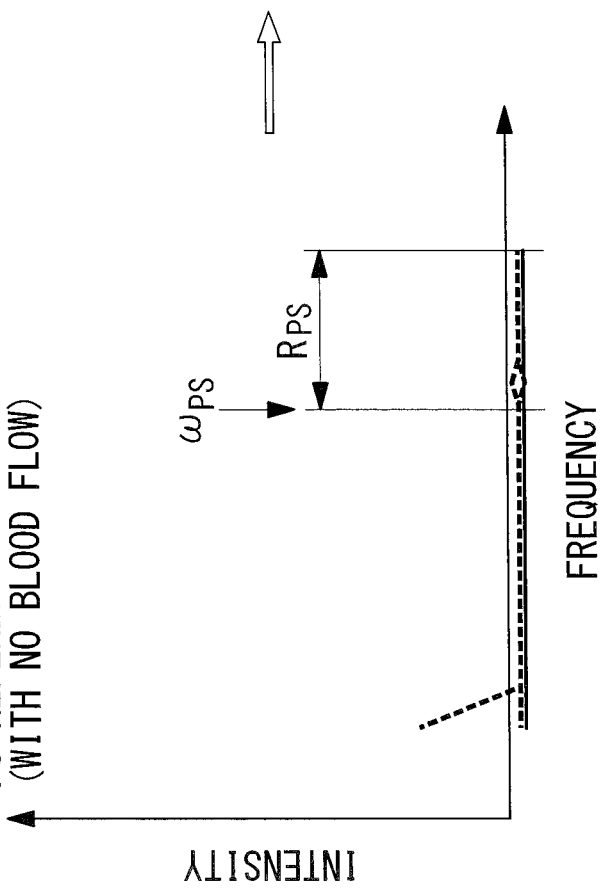
Figure 15B:
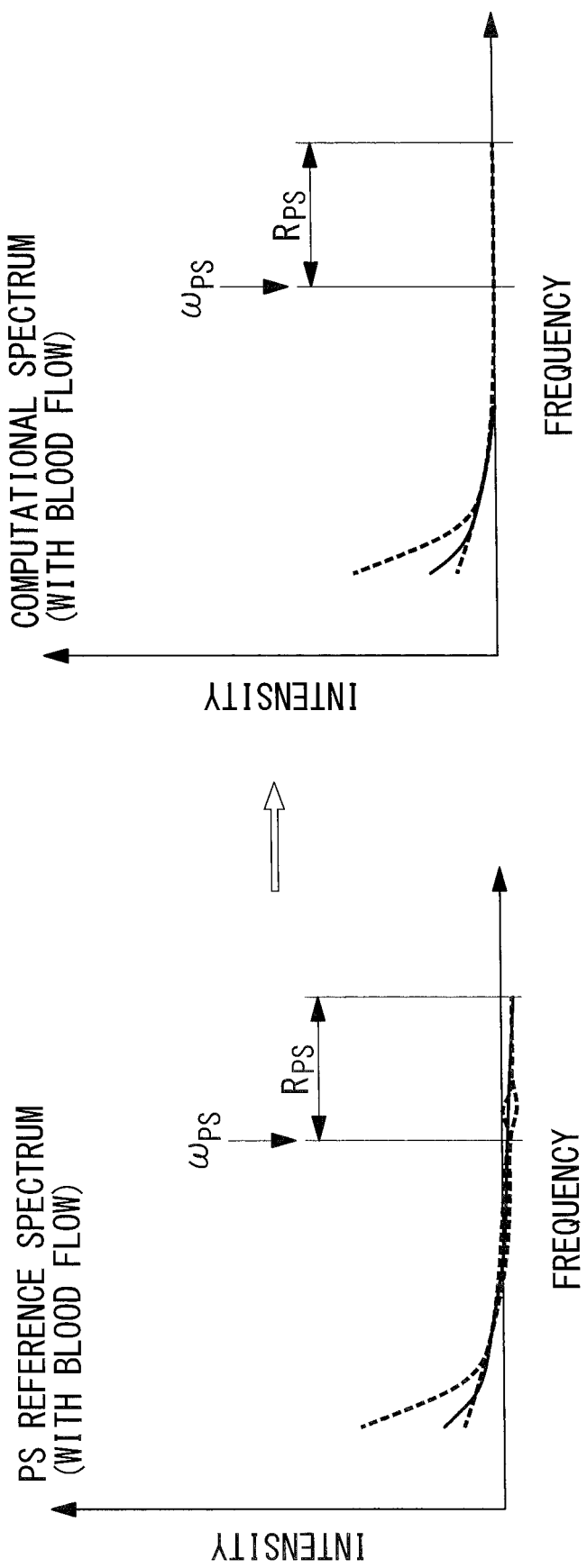
FIG. 15B is a view showing the relationship between the PS reference spectrum and a computational spectrum in a case in which a blood flow exists.

Furthermore, as shown in FIGS. 14A and 14B, a PS reference frequency $\omega_{PS}$ that is lower than spike noise at the lowest frequency is set, and a maximum value $\max_{PS}$ of the region spectrum $f_{rng}$ in a PS reference region $R_{PS}$ that is higher than the PS reference frequency $\omega_{PS}$ is subtracted from the region spectrum $f_{rng}$, thereby calculating a PS reference spectrum $f_{PS}(\omega)$ (Step S8). Then, in the PS reference spectrum $f_{PS}(\omega)$, because elements having negative intensities are produced by subtracting the maximum value $\max_{PS}$ of the region spectrum $f_{rng}$, the negative intensities are replaced with 0 in a region having the negative intensities, thereby calculating a computational spectrum $f_C(\omega)$ in which the all intensities are equal to or higher than 0, as shown in FIGS. 15A and 15B (Steps S9 to S11).

Then, the calculated computational spectrum $f_C(\omega)$ and the resultant obtained by multiplying the computational spectrum $f_C(\omega)$ by the frequency $\omega$ are integrated with respect to the frequency $\omega$ in the integration region $R_{Int}$, thus obtaining two integral values $I_f$ and $I_{\omega f}$ (Step S12).

Here, it is determined whether the integral value $I_f$ of the computational spectrum is 0 (Step S13), and, if the integral value $I_f$ is 0, it is replaced with 1 for convenience (Step S14). Accordingly, division by using 0 is avoided. Furthermore, it is determined whether the integral value $I_f$ of the computational spectrum is larger than a predetermined integral cut-off value $I_{fCUT}$ (Step S15). According to the determination result, the average frequency is calculated as follows.

If $I_f > I_{fCUT}, \omega_{ave} = I_{\omega f}/I_f$

If $I_f \leq I_{fCUT}, \omega_{ave} = 0$

Specifically, if the integral value $I_f$ is equal to or lower than the cut-off value $I_{fCUT}$, there is a possibility that erroneous determination will be made because of the random noise that could not be completely removed in the upper step. Thus, only if the integral value $I_f$ is larger than the cut-off value $I_{fCUT}$, the average frequency $\omega_{ave}$ is calculated (Step S16), and, if the integral value $I_f$ is equal to or lower than the cut-off value $I_{fCUT}$, the average frequency $\omega_{ave}$ is not calculated and is set to 0 (Step S17), thus preventing erroneous determination.

Then, it is determined whether the calculated value of the average frequency $\omega_{ave}$ is larger than a predetermined average-frequency threshold (first threshold) $\omega_{th}$ (Step S18). If the calculated value of the average frequency $\omega_{ave}$ is larger than the predetermined average-frequency threshold (first threshold) $\omega_{th}$, there exists a blood flow faster than a desired flow rate, thus generating a determination result $S_{TRUE}$ indicating that a relatively thick blood vessel B exists (Step S19). On the other hand, if the average frequency equal to or lower than the average-frequency threshold $\omega_{th}$, a determination result $S_{FALSE}$ indicating that a thick blood vessel B does not exist is generated (Step S20). Then, a signal indicating one of the determination results is output from the determination unit 14 (Step S21).

When the determination unit 14 determines that the detection-target blood vessel B does not exist, the control unit 3 causes the energy supply unit 6 to supply the energy source having a high intensity to the energy action portion 5, thereby actuating the energy action portion 5 in the incision mode. On the other hand, when the determination unit 14 determines that the detection-target blood vessel B exists, the control unit 3 causes the energy supply unit 6 to supply the energy source having a lower intensity than the energy source used in the incision mode, to the energy action portion 5, thereby actuating the energy action portion 5 in the coagulation mode.

To treat the living tissue A by using the above-described surgical treatment device, a treatment target site of the living tissue A is gripped between the pair of jaws 7 and 8. The treatment target site between the jaws 7 and 8 is irradiated with the laser light L from the light emitting part 10, and scattered light S of the laser light L that has been transmitted through the treatment target site while being scattered by the living tissue A is received by the light receiving part 11. The received scattered light S is detected by the light detection unit 12, and the time-series data of the scattered light S is generated in the frequency analysis unit 13. In the frequency analysis unit 13, the average frequency $\omega_{ave}$ of the real-time Doppler spectrum $f_{RT}(\omega)$ is extracted through frequency analysis of the time-series data, and the determination unit 14 determines whether a detection-target blood vessel B that has a diameter falling within a predetermined range exists in the living tissue A, on the basis of the average frequency $\omega_{ave}$.

If it is determined that the detection-target blood vessel B does not exist in the treatment target site, the control unit 3 actuates the energy action portion 5 in the incision mode, thereby supplying high energy from the jaws 7 and 8 to the treatment target site and incising the treatment target site. If it is determined that the detection-target blood vessel B exists in the treatment target site, the control unit 3 actuates the energy action portion 5 in the coagulation mode, thereby supplying low energy from the jaws 7 and 8 to the treatment target site and coagulating the treatment target site.

In this way, according to this embodiment, the Doppler shift of the scattered light S, which is caused by a blood flow in the blood vessel B, is analyzed, thereby detecting blood flowing in the blood vessel B while clearly distinguishing it from blood leaking from the blood vessel B due to bleeding. Accordingly, there is an advantage that it is possible to accurately detect the blood vessel B existing in the living tissue A.

Furthermore, by using the fact that the magnitude of the average frequency $\omega_{ave}$ depends on the thickness of the blood vessel B, it is possible to recognize not only the presence or absence of the blood vessel B but also the thickness of the blood vessel B. Accordingly, there is an advantage that only a thick blood vessel B is detected, thus making it possible to appropriately control the actuation of the energy action portion 5 so as to reliably avoid incision of a treatment target site where the thick blood vessel B exists.

Furthermore, in this embodiment, in the determination in the determination unit 14, the low-frequency noise, the noise floor, the spike noise, and the random noise included in the real-time Doppler spectrum $f_{RT}(\omega)$ are effectively removed, and the average frequency $\omega_{ave}$ is calculated; therefore, the existence of a thick blood vessel B can be accurately determined. Accordingly, it is possible to prevent erroneous determination that would be caused by the noise and to appropriately control the actuation of the energy action portion 5 so as to reliably avoid incision of a treatment target site where a thick blood vessel B exists.

Note that, in this embodiment, when the determination unit 14 determines that the detection-target blood vessel B exists, the control unit 3 may display, for the surgeon, a sign indicating the existence of the detection-target blood vessel B, on a display unit (not shown), or may output a sound from a speaker (not shown). By doing so, the existence of the detection-target blood vessel B in the treatment target site can be reliably recognized by the surgeon.

Furthermore, in this embodiment, instead of controlling the intensity of the energy source to be supplied from the energy supply unit 6 to the energy action portion 5, the control unit 3 may stop supplying the energy source from the energy supply unit 6 to the energy action portion 5 when the determination unit 14 determines that the detection-target blood vessel B exists and may allow the energy source to be supplied from the energy supply unit 6 to the energy action portion 5 when the determination unit 14 determines that the detection-target blood vessel B does not exist.

By doing so, the action of the energy on the detection-target blood vessel B can be reliably avoided.

Figure 16:
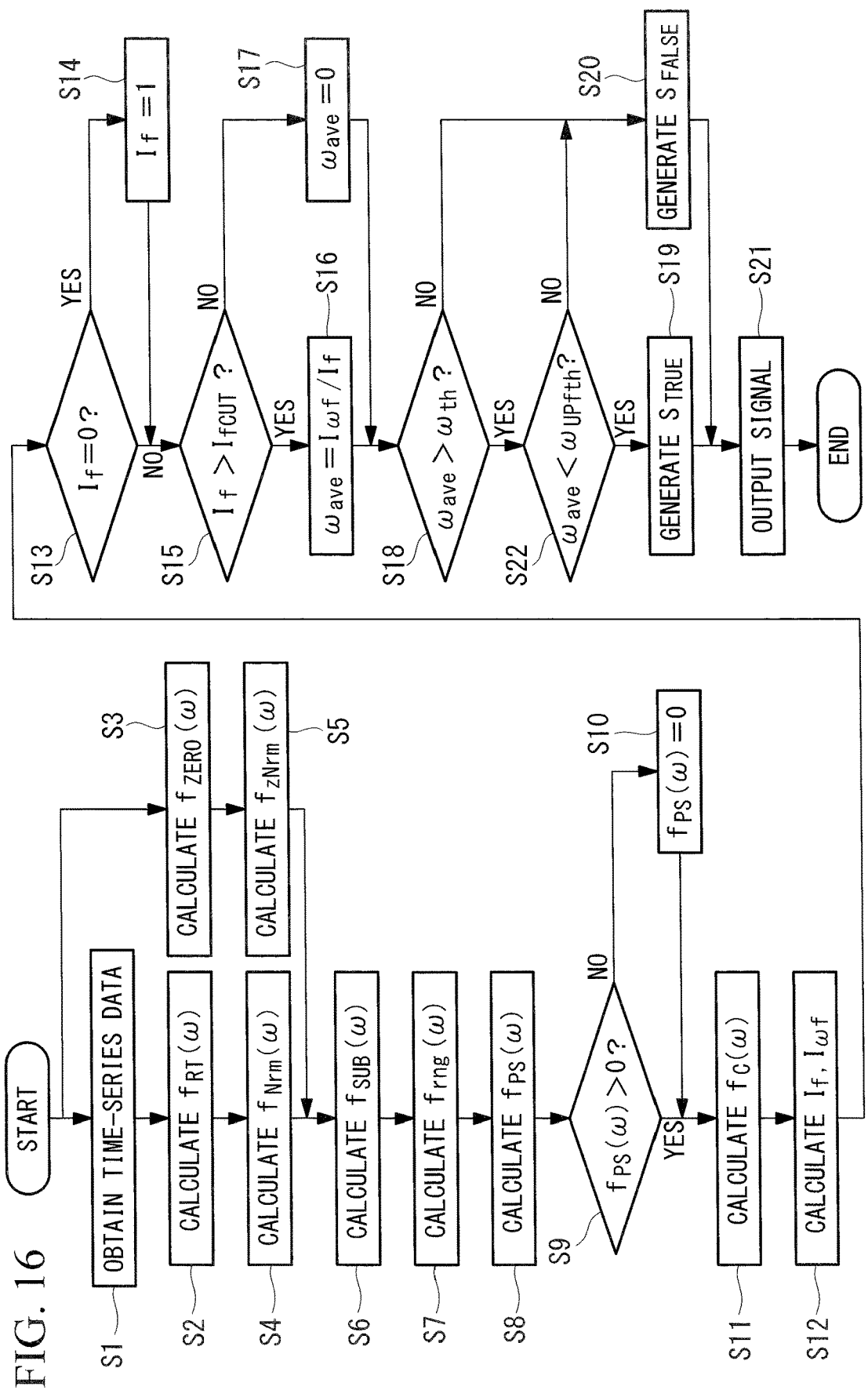
FIG. 16 is a flowchart showing a modification of the blood-vessel recognition blood-flow measurement method shown in FIG. 2.

Furthermore, in this embodiment, although it is determined that the thick blood vessel B exists when the calculated average frequency $\omega_{ave}$ is larger than the predetermined threshold $\omega_{th}$, as shown in FIG. 16, an upper threshold (second threshold) $\omega_{UPth}$ may be further adopted, and, when the average frequency $\omega_{ave}$ is equal to or larger than the upper threshold $\omega_{UPth}$, the existence of the thick blood vessel B may not be determined (Step S22). In the case in which the blood flow rate is determined on the basis of the real-time Doppler spectrum $f_{RT}(\omega)$, when the blood flow rate decreases, the random noise becomes dominant, thus making it impossible to completely remove the noise floor in the upper step. Thus, by doing such processing, it is possible to prevent erroneous determination due to the random noise that could not be completely removed in the upper step.

As a result, the above-described embodiment leads to the following aspect.

According to one aspect, the present invention provides a blood-vessel recognition blood-flow measurement method including: a step of obtaining a real-time Doppler spectrum by performing a Fourier transform on a temporal waveform of the intensity of scattered light produced when laser light is radiated onto a living body; a step of calculating a normalized real-time Doppler spectrum by normalizing the real-time Doppler spectrum by using an average value of the real-time Doppler spectrum in a predetermined normalized region; a step of calculating a normalized zero spectrum by normalizing a zero spectrum measured when laser light is radiated in a state in which a blood flow does not exist, by using an average value of the zero spectrum in a normalized region; a step of calculating a subtracted spectrum by subtracting the normalized zero spectrum from the normalized real-time Doppler spectrum; a step of calculating a region spectrum by extracting, from the subtracted spectrum, a region for integration by using a predetermined integration region; a step of calculating a PS reference spectrum by subtracting, from the region spectrum, the maximum value of the region spectrum in a predetermined PS reference region; a step of obtaining a computational spectrum by replacing an element of which the PS reference spectrum is negative with zero; a step of calculating an average frequency on the basis of the computational spectrum; and a step of determining a blood flow velocity by comparing the calculated average frequency with a predetermined threshold.

According to this aspect, a real-time Doppler spectrum is obtained by performing a Fourier transform on a temporal waveform of the intensity of scattered light of laser light in living body, and the obtained real-time Doppler spectrum is normalized by using the average value in a normalized region, thus calculating a normalized real-time Doppler spectrum. On the other hand, a zero spectrum is separately obtained by performing a Fourier transform on a temporal waveform of the intensity of scattered light obtained by radiating laser light in a state in which there is no blood flow, and the zero spectrum is normalized by using the average value in the normalized region, thus calculating a normalized zero spectrum. Adopted as the normalized region is an arbitrary frequency region set at a frequency higher than a frequency at which the intensity of the real-time Doppler spectrum corresponding to a desired blood flow becomes the same level as the intensity of a noise floor.

Then, the normalized zero spectrum is subtracted from the normalized real-time Doppler spectrum, thereby calculating a subtracted spectrum in which the noise floor and spike noise are reduced. A region for integration is extracted from this subtracted spectrum, thereby calculating a region spectrum in which low-frequency noise is reduced. Then, the maximum value in the PS reference region is subtracted from the region spectrum, thereby calculating a PS reference spectrum in which random noise and spike noise are reduced.

Because an element of which the intensity becomes lower than zero is produced only by subtracting the maximum value from the region spectrum, the portion where the intensity has become lower than zero is replaced with 0, thereby calculating a computational spectrum having intensity equal to or higher than zero.

Then, an average frequency is calculated on the basis of the computational spectrum calculated in this way. Because the average frequency is increased according to the velocity of the blood flow, it is possible to determine the thickness of a blood vessel on the basis of the average frequency.

Specifically, according to this aspect, the average frequency is calculated on the basis of the computational spectrum, in which the low-frequency noise, the noise floor, the spike noise, and the random noise included in the real-time Doppler spectrum are removed, it is possible to accurately determine the thickness of a blood vessel existing in living body.

In the above-described aspect, in the step of determining the blood flow velocity by comparing the calculated average frequency with the predetermined threshold, it may be determined that a blood vessel exists when the average frequency is larger than a predetermined first threshold.

By doing so, only when the average frequency is larger than the first threshold, and the blood flow is relatively large, it is determined that a blood vessel exists; thus, because attention is prevented from being called to a site where only a small blood vessel exists, treatment can be smoothly performed.

Furthermore, in the above-described aspect, in the step of determining the blood flow velocity by comparing the calculated average frequency with the predetermined threshold, it may be determined that a blood vessel exists when the average frequency is smaller than a predetermined second threshold that is larger than the first threshold.

By doing so, when the intensity of scattered light of laser light in living body is low, if the average frequency is larger than the second threshold, it is determined that a blood vessel does not exist; thus, because attention is more accurately prevented from being called to a site where only a small blood vessel exists, treatment can be more smoothly performed.

Furthermore, in the above-described aspect, the step of calculating the average frequency may include: a step of obtaining, in a predetermined integration region, frequency integral values of the computational spectrum and of a spectrum that is obtained by multiplying the computational spectrum by a frequency; a step of comparing a predetermined integral cut-off value with the frequency integral value of the computational spectrum; and a step of setting, as a result of the comparison, the average frequency on the basis of the following expressions:

if $I_f > I_{fCUT}, \omega_{ave} = I_{\omega f}/I_f$; and if $I_f \leq I_{fCUT}, \omega_{ave} = 0$.

By doing so, the average frequency is calculated only when the frequency integral value of the computational spectrum is larger than the predetermined integral cut-off value, and the average frequency is set to zero when the frequency integral value is equal to or lower than the integral cut-off value; therefore, it is possible to prevent the accuracy of determination of a blood vessel from being reduced by the noise floor, which cannot be completely removed due to the random noise.

According to the present invention, an advantageous effect is afforded in that it is possible to accurately detect a blood vessel existing in living tissue and to selectively detect a blood vessel having a predetermined thickness.

REFERENCE SIGNS LIST

B blood vessel
L laser light
$f_{RT}(\omega)$ real-time Doppler spectrum
$R_{Nrm}$ normalized region
$f_{Nrm}(\omega)$ normalized real-time Doppler spectrum
$f_{ZERO}(\omega)$ zero spectrum
$f_{zNrm}(\omega)$ normalized zero spectrum
$f_{SUB}(\omega)$ subtracted spectrum
$f_{rng}(\omega)$ region spectrum
$R_{PS}$ PS reference region
$f_{PS}(\omega)$ PS reference spectrum
$f_C(\omega)$ computational spectrum
$R_{Int}$ integration region
$\omega_{ave}$ average frequency
$\omega_{th}$ average-frequency threshold (first threshold)
$\omega_{UPth}$ upper threshold (second threshold)
$\omega_{PS}$ PS reference frequency
$I_f$ integral value of computational spectrum
$I_{\omega f}$ integral value when resultant obtained by multiplying computational spectrum $f_C(\omega)$ by frequency $\omega$ is integrated with respect to frequency $\omega$ in integration region $R_{Int}$
$I_{fCUT}$ integral cut-off value

The invention claimed is:

1. A blood-vessel recognition blood-flow measurement method comprising:
   obtaining a real-time Doppler spectrum by performing a Fourier transform on a temporal waveform of an intensity of scattered light produced when laser light is radiated onto a living body;
   setting, as a first frequency region, a frequency range higher than a frequency at which an intensity of the real-time Doppler spectrum becomes a same level as a noise floor intensity;
   calculating a normalized real-time Doppler spectrum by normalizing the real-time Doppler spectrum with an average value of the real-time Doppler spectrum in the first frequency region;
   calculating a normalized zero spectrum by normalizing a zero spectrum measured when laser light is radiated in a state in which a blood flow does not exist, with the average value of the zero spectrum in the first frequency region;
   calculating a subtracted spectrum by subtracting the normalized zero spectrum from the normalized real-time Doppler spectrum;

setting, as a second frequency region, a frequency range in which a low-frequency noise can be removed;

calculating a region spectrum by removing, from the subtracted spectrum, a spectrum in a frequency region lower than the second frequency region;

setting, as a third frequency region, a frequency range including a spike noise in the region spectrum;

calculating a PS reference spectrum by subtracting, from the region spectrum, the maximum value of the region spectrum in the third frequency region;

obtaining a computational spectrum by replacing an element of which the PS reference spectrum is negative with zero;

calculating an average frequency based on the computational spectrum; and determining a blood flow velocity according to the calculated average frequency.

2. A blood-vessel recognition blood-flow measurement method according to claim 1, wherein, the determining of the blood flow velocity comprises determining that a blood vessel exists, in response to the average frequency being larger than a predetermined first threshold.

3. A blood-vessel recognition blood-flow measurement method according to claim 2, wherein the determining of the blood flow velocity comprises determining that a blood vessel exists, in response to the average frequency being smaller than a predetermined second threshold that is larger than the first threshold.

4. A blood-vessel recognition blood-flow measurement method according to claim 1, wherein the calculating of the average frequency comprises:

obtaining, in the second frequency region, frequency integral values of the computational spectrum and of a spectrum that is obtained by multiplying the computational spectrum by a frequency;

comparing a predetermined integral cut-off value with the frequency integral value of the computational spectrum; and setting, as a result of the comparison, the average frequency based on the following expressions:

if $I_f > I_{fCUT}, \omega_{ave} = I_{\omega f}/I_f$; and if $I_f \leq I_{fCUT}, \omega_{ave} = 0$.

* * * * *